(12) United States Patent
Jang et al.

(10) Patent No.: US 11,371,970 B2
(45) Date of Patent: Jun. 28, 2022

(54) METHOD FOR ANALYZING MOLECULAR WEIGHT OF EACH COMPONENT OF POLYMER COMPOUND, AND ANALYSIS SYSTEM USED THEREFOR

(71) Applicant: LG Chem, Ltd., Seoul (KR)

(72) Inventors: Rin Jang, Daejeon (KR); Byoung Hyoun Kim, Daejeon (KR)

(73) Assignee: LG Chem, Ltd.

( * ) Notice: Subject to any disclaimer, the term of this patent is extended or adjusted under 35 U.S.C. 154(b) by 213 days.

(21) Appl. No.: 16/769,399

(22) PCT Filed: Sep. 16, 2019

(86) PCT No.: PCT/KR2019/011912
§ 371 (c)(1),
(2) Date: Jun. 3, 2020

(87) PCT Pub. No.: WO2020/055207
PCT Pub. Date: Mar. 19, 2020

(65) Prior Publication Data
US 2021/0172914 A1    Jun. 10, 2021

(30) Foreign Application Priority Data

Sep. 12, 2018  (KR) .................. 10-2018-0109018
Sep. 11, 2019  (KR) .................. 10-2019-0112999

(51) Int. Cl.
*G01N 30/72*     (2006.01)
*G01N 30/86*     (2006.01)
(Continued)

(52) U.S. Cl.
CPC ..... *G01N 30/7206* (2013.01); *G01N 30/8631* (2013.01); *G01N 30/88* (2013.01); *G01N 2030/025* (2013.01)

(58) Field of Classification Search
CPC ........ G01N 30/02; G01N 1/405; G01N 27/62; G01N 2030/027; G01N 2560/00;
(Continued)

(56) References Cited

U.S. PATENT DOCUMENTS 5,130,538 A * 7/1992 Fenn ................... H01J 49/4225
250/288
2005/0255606 A1 * 11/2005 Ahmed .............. G06K 9/00503
436/173
(Continued)

FOREIGN PATENT DOCUMENTS

| JP | H90257780 A | 10/1997 |
|----|----|----|
| JP | H10038871 A | 2/1998 |

(Continued)

OTHER PUBLICATIONS

International Search Report from Application No. PCT/KR2019/011912 dated Jan. 30, 2020, 2 pages.
(Continued)

*Primary Examiner* — David A Vanore
(74) *Attorney, Agent, or Firm* — Lerner, David, Littenberg, Krumholz & Mentlik, LLP (57) ABSTRACT

The present invention relates to a method for analyzing the molecular weight of each polymer comprised in a polymer compound, and an analysis system used therefor. More specifically, the present invention relates to an analysis method of components of polymer compounds and molecular weight by component using a system in which size-exclusion chromatography (SEC)-pyrolysis gas chromatography (Py-GC)-mass spectrometry (MS) are connected in series and to an analysis system used in the method.

13 Claims, 6 Drawing Sheets

(51) Int. Cl.
*G01N 30/88* (2006.01)
*G01N 30/02* (2006.01)
(58) Field of Classification Search
CPC ............... G01N 30/72; G01N 30/88; G01N 2030/8827; C12N 15/1017
See application file for complete search history.

(56) References Cited

U.S. PATENT DOCUMENTS

2014/0275501 A1* 9/2014 Capanema ............... C07G 1/00
 530/500
2021/0172914 A1* 6/2021 Jang ................... G01N 30/8631

FOREIGN PATENT DOCUMENTS

| JP | 2004325265 A | 11/2004 |
| JP | 2006084261 A | 3/2006 |
| KR | 20160037512 A | 4/2016 |

OTHER PUBLICATIONS

Kaal et al., "On-line SEC-Py-GC-MS for the Automated Comprehensive Characterization of Copolymers", Coupling Matters, LCGC Europe, Sep. 2007, vol. 20, No. 9, pp. 444-452.
Kaal et al., "On-line size exclusion chromatography-pyrolysis-gas chromatography-mass spectrometry for copolymer characterization and additive analysis", Journal of Chromatography, Dec. 2006, vol. 1143, pp. 182-189.

* cited by examiner

METHOD FOR ANALYZING MOLECULAR WEIGHT OF EACH COMPONENT OF POLYMER COMPOUND, AND ANALYSIS SYSTEM USED THEREFOR

CROSS-REFERENCE TO RELATED APPLICATIONS

The present application is a national phase entry under 35 U.S.C. § 371 of International Application No. PCT/KR2019/011912, filed Sep. 16, 2019, which claims priority to Korean Patent Application Nos. 10-2018-0109018, filed on Sep. 12, 2018 and Korean Patent Application No. 10-2019-0112999, filed on Sep. 11, 2019, the entire disclosures of which are incorporated by reference herein.

BACKGROUND OF THE INVENTION

1. Field of the Invention

The present invention relates to an analysis method of components and molecular weight of polymer compounds and an analysis system used in the method. More specifically, the present invention relates to an analysis method of components of polymer compounds and molecular weight by component using a system in which size-exclusion chromatography (SEC)-pyrolysis gas chromatography (Py-GC)-mass spectrometry (MS) are connected in series and to an analysis system used in the method.

2. Description of the Related Art

Polymer compounds are prepared by blending heterogeneous polymers in a molten state. They are used in various fields because they can realize various physical properties other than the physical properties of unit polymers by blending heterogeneous polymers. Since the physical properties of the polymer compound are greatly influenced by the molecular weight and molecular weight distribution of the unit polymer blended into the polymer compound, the analysis of molecular weight and molecular weight distribution by component of the polymer compound is very important for predicting the physical properties of the polymer compound.

In general, the molecular weight of the polymer can be determined using size-exclusion chromatography (SEC) in which the material is separated according to the size of the molecule (molecular weight). On the other hand, in order to measure the monomer content ratio of the polymer and to confirm the structure of the polymer, there is used an analysis method using nuclear magnetic resonance (NMR), infrared spectroscopy (IR spectroscopy), scanning electron microscope (SEM) and the like.

However, the above methods have a limitation in that for the polymer compound having two or more kinds of unit polymers of different molecular weight or monomer content ratio mixed, it should be separated into unit polymer in order to determine each molecular weight. Therefore, there is a need for a method that can determine molecular weight according to each polymer component of the polymer compound by a simpler method.

SUMMARY OF THE INVENTION

An object of the present invention is to provide an analysis method of molecular weight of each unit polymer in a polymer compound having two or more kinds of unit polymers.

In order to achieve the above object, the present invention provides an analysis method of molecular weight of unit polymer contained in a polymer compound, comprising the steps of:

(A) injecting a sample of the polymer compound into size exclusion chromatography (SEC), and collecting the sample passed through it at a predetermined time interval;

(B) introducing the sample collected in the step (A) directly into pyrolysis gas chromatography (Py-GC)-mass spectrometry (MS) which is connected to the size exclusion chromatography, thereby obtaining a mass spectrum;

(C) normalizing each peak area of the mass spectrum obtained in the step (B) to obtain a relative content ratio of monomer constituting the unit polymer;

(D) obtaining from the relative content ratio of monomer a graph of relative content ratio according to collection time as a raw data;

(E) deconvoluting peak points of the raw data to a probability density function of Gaussian distribution to obtain a deconvolution graph; and (F) obtaining a cumulative fit peak chromatogram from the deconvolution graph and substituting the cumulative fit peak chromatogram into a calibration curve of a standard to calculate molecular weight of each unit polymer.

In addition, the present invention provides an analysis system used in the analysis of molecular weight of unit polymer contained in a polymer compound, comprising:

a size exclusion chromatography into which the sample is injected;

a sample collection and injection device for automatically collecting the sample passed through the size exclusion chromatography at a predetermined time interval and injecting the sample into a subsequent device;

a pyrolyzer in which the collected sample is injected and pyrolyzed; and a gas chromatography and mass spectrometer into which the pyrolyzed sample is injected.

Effect of the Invention

According to the present invention, the molecular weight of each of the unit polymers can be measured by a simple method without separating polymer compounds having two or more kinds of unit polymers into each unit polymer.

DETAILED DESCRIPTION OF THE INVENTION

Hereinafter, the present invention will be described in detail.

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

According to the conventional analysis method of polymers, size exclusion chromatography (SEC) provides only total molecular weight of polymer compounds, and pyrolysis gas chromatography (Py-GC)-mass spectrometry (MS) provide only monomer content ratio of polymer compounds.

In this regard, the present applicant has proposed an analysis method of monomer content according to molecular weight of a polymer compound having heterogeneous polymers of various molecular weights in Korean Patent Application No. 10-2018-0108078, entire disclosure of which is incorporated herein by reference.

The present invention provides a method for identifying molecular weight distribution and molecular weight of unit polymer for a polymer compound having heterogeneous polymers of various molecular weights.

Here, the heterogeneous polymer contained in the polymer compound refers to a resin in which two or more unit polymers are blended. The unit polymer to be blended may be a homopolymer or a copolymer. The molecular weight of each unit polymer can be calculated as long as the unit polymer is pyrolyzed to identify the monomer component regardless of whether the unit polymer is a homopolymer or a copolymer.

In one embodiment, the present invention provides an analysis method of molecular weight of unit polymer contained in a polymer compound, comprising the steps of:

(A) injecting a sample of the polymer compound into size exclusion chromatography (SEC), and collecting the sample passed through it at a predetermined time interval;

(B) introducing the sample collected in the step (A) directly into pyrolysis gas chromatography (Py-GC)-mass spectrometry (MS) which is connected to the size exclusion chromatography, thereby obtaining a mass spectrum;

(C) normalizing each peak area of the mass spectrum obtained in the step (B) to obtain a relative content ratio of monomer constituting the unit polymer;

(D) obtaining from the relative content ratio of monomer a graph of relative content ratio according to collection time as a raw data;

(E) deconvoluting peak points of the raw data to a probability density function of Gaussian distribution to obtain a deconvolution graph; and (F) obtaining a cumulative fit peak chromatogram from the deconvolution graph and substituting the cumulative fit peak chromatogram into a calibration curve of a standard to calculate molecular weight of each unit polymer.

The probability density function of Gaussian distribution is represented by Equation 1 below, and may be calculated by commercially obtainable software, for example, Origin program of OriginLab Corporation.

$$f(x|\mu, \sigma^2) = \frac{1}{\sqrt{2\pi\sigma^2}} e^{-\frac{(x-\mu)^2}{2\sigma^2}} \quad \text{[Equation 1]}$$

In Equation 1,
μ is a mean,
σ is a standard deviation,
$\sigma^2$ is a variance.

In one embodiment, the normalization in the step (C) is to analyze the sample to be analyzed by NMR or Py-GC/MS to obtain a total content ratio of monomers, and to determine a relative content ratio from the relative area of each peak based on the total content ratio of monomers when the sum of peak areas of the mass spectrum obtained in the step (B) is set to 100.

For example, if the sample is identified to have MMA and styrene in a 50:50 weight ratio as analyzed by NMR or Py-GC/MS, a relative content ratio of each monomer can be obtained from a relative area of MMA peak according to the collection time and a relative area of styrene peak according to the collection time, under the condition that the sum of peak areas obtained from the mass spectrum is set to 100 and a ratio of a total area of MMA peak to a total area of styrene peak is 50:50.

In one embodiment, the sample in the step (A) may be automatically collected at an interval of from 5 seconds to 600 seconds. For example, collecting intervals may be at least 10 seconds, at least 15 seconds, at least 20 seconds, at least 25 seconds, and at most 500 seconds, at most 400 seconds, at most 300 seconds, at most 200 seconds, at most 100 seconds, at most 50 seconds, or about 30 seconds.

Samples passed through size exclusion chromatography (SEC) in the step (A) are automatically collected and consecutively injected into a subsequent analyzer (Py-GC/MS). According to one embodiment, PAL RTC from CTC Analytic may be used as an automatic preparation and injection device.

In one embodiment, the unit polymer contained in the polymer compound in the step (A) may comprise two or more kinds of polymers having different weight average molecular weight or number average molecular weight.

In a further embodiment, the unit polymer contained in the polymer compound in the step (A) may be a homopolymer or a copolymer.

In another embodiment, the polymer compound in the step (A) has a bimodal or multimodal molecular weight distribution.

In one embodiment, oxygen-containing organic compounds are used as a mobile phase of size exclusion chromatography in the step (A) at a flow rate of 0.005 to 10 mL/min. In a preferred embodiment, the flow rate may be at least 0.01 mL/min, at least 0.1 mL/min or at least 0.5 mL/min, and at most 5 mL/min, at most 3 mL/min or at most 2 mL/min, or at most 1 mL/min.

In one embodiment, the mobile phase is tetrahydrofuran (THF).

In one embodiment, Ar or He is used as a carrier gas in the step (B).

In one embodiment, the pyrolysis in the step (B) is performed at 500 to 800° C. at a temperature increase rate of 50 to 80° C./sec. In a preferred embodiment, the pyrolysis may be performed at 550 to 700° C. or at about 600° C. at a temperature increase rate of 50 to 70° C./sec, or about 60° C./sec.

In addition, in the step (B), the gas chromatography may be carried out with starting at an oven temperature of 40 to 60° C. or of about 50° C., increasing the temperature at a rate of 10 to 20° C./min or about 15° C./min, and then maintaining the temperature at 300 to 400° C. or at 320° C. in 5 to 20 minutes or in about 10 minutes.

The calculating molecular weight by substituting into the calibration curve of a standard in the step (F) is commonly known as a method of calculating the molecular weight of the polymer. As a standard, polystyrene, PMMA, PEG/PEO, polysaccharide, polyacrylic acid, polystyrene sulfonic acid, etc. can be used. Polystyrene is generally used as a standard.

According to the present invention, the following advantages are provided.

(1) It is possible to analyze molecular weight of unit polymer contained in the polymer compound. It is possible to analyze molecular weight of each resin component in the resin sample with bimodal or higher molecular weight distribution.

(2) It is possible to determine molecular weight distribution of unit polymer contained in polymer compound via analysis of a single polymer compound sample.

It is possible to obtain desired analytical information in a simple way by analyzing a single polymer compound sample with an automated system including a size exclusion chromatography (SEC), an automatic sample preparation and injection device (PAL RTC), a pyrolyzer, a gas chromatography and a mass spectrometer.

In addition, the present invention provides an analysis system used in the analysis of molecular weight of unit polymer contained in a polymer compound, comprising a size exclusion chromatography into which the sample is injected; a sample collection and injection device for automatically collecting the sample passed through the size exclusion chromatography at a predetermined time interval and injecting the sample into a subsequent device; a pyrolyzer in which the collected sample is injected and pyrolyzed; and a gas chromatography and mass spectrometer into which the pyrolyzed sample is injected.

In one embodiment, the size exclusion chromatography may comprise one column having a length of 30 to 100 mm and an inner diameter of 5 to 10 mm and filled with particles having a particle diameter of 5 to 20 μm, and the columns having a length of 200 to 500 mm and an inner diameter of 5 to 10 mm and filled with particles having a particle diameter of 5 to 20 μm.

In a preferred embodiment, the size exclusion chromatography may comprise one column having a length of 40 to 60 mm or about 50 nm and an inner diameter of 6 to 8 mm or about 7.5 mm and filled with particles having a particle diameter of 8 to 12 μm or about 10 μm, and two columns having a length of 250 to 400 mm or about 300 mm and an inner diameter of 6 to 8 mm or about 7.5 mm and filled with particles having a particle diameter of 8 to 12 μm or about 10 μm.

In one embodiment, the gas chromatography may comprise a column having a length of 20 to 50 m, an inner diameter of 0.1 to 0.5 mm, and a thickness of 0.1 to 0.5 μm. In a preferred embodiment, the gas chromatography comprises a column having a length of 20 to 40 m or about 30 m, an inner diameter of 0.2 to 0.4 mm or 0.2 to 0.3 mm, and a thickness of 0.2 to 0.4 μm or 0.2 to 0.3 μm.

Hereinafter, preferred examples are provided to help the understanding of the present invention, but the following examples are merely illustrative of the present invention, and various changes and modifications within the scope and spirit of the present invention are apparent to those skilled in the art. It is natural that such changes and modifications fall within the scope of the appended claims.

Analytical Equipment and Conditions

Equipments and conditions of size exclusion chromatography, pyrolysis gas chromatography and mass spectrometry used in this example are as follows.

(1) Size Exclusion Chromatography

Analysis was performed using Prominence HPLC system of Shimadzu (CBM-20A/LC-20AD/DGU-20A3R/CTO-20AC/SIL-20AC/RID-20A). As a column, one PLgel MIXED guard column (length 50 mm, I.D.7.5 mm, particle size: 10 μm) and two PLgel MIXED-B columns (length 300 mm, I.D.7.5 mm, particle size: 10 μm) of Agilent were used at 40° C. As a mobile phase, the degassed tetrahydrofuran (for HPLC, J.T. Baker) was used at a flow rate of 1.0 mL/min. The injection volume of the sample was 50 μL.

(2) Pyrolysis Gas Chromatography-Mass Spectrometer

Analysis was performed using OPTIC-4S and GCMS-QP2020 of Shimadzu. As a column, a Rxi™-5 ms column having a length of 30 m, an I.D. of 0.25 mm and a thickness 0.25 μm was used. As a mobile phase gas, helium (He) was used at a flow rate of 1 ml/min. The sample injection volume was 10 μL. After injection of the sample, the solvent was removed by purging at 150 mL/min at 100° C. for 1 minute. After removal of the solvent, the inlet temperature was raised at a rate of 60° C./s and pyrolysis was carried out at 600° C. for 10 seconds. A flow rate of gas chromatography was 1 mL/min, a split ratio was 1/20, and an interface temperature of mass spectrometer was 300° C. An oven temperature of gas chromatography was started at 50° C. and then increased to 320° C. at a rate of 15° C./min and maintained for 10 minutes to obtain a chromatogram.

(3) Sample to be Analyzed and Standard Product

As a sample to be analyzed, a compound in which high molecular weight polystyrene (900,000 Daltons, Sigma-Aldrich), high molecular weight polymethylmethacrylate (1 Million Daltons, PA912, LG CHEM), low molecular weight polystyrene (90,000 Daltons, Sigma-Aldrich) and low molecular weight polymethylmethacrylate (average Mw ~120,000, Sigma-Aldrich) were blended in a weight ratio of 1:4:4:1 were used. Therefore, the specification of the sample used is MMA:Styrene 50:50 (weight ratio).

A standard for analysis of relative molecular weight by SEC were 4230000, 9560000, 316500, 70950, 31400, 8450, 3940, 580 Da polystyrene from Polymer standard service and Shodex. The calibration curve obtained from analysis of the standard has f $(x)=0.001214223x_3-0.535420x_2+0.2225834x+9.246424$.

MMA:styrene 50:50 (weight ratio) was used as a standard for analysis of monomer content using Py-GC/MS. At this time, the content ratio of the monomer obtained by analyzing by NMR or Py-GC/MS can be applied for analyzing a sample with unknown monomer content.

EXAMPLE

In this example, the molecular weight of unit polymer contained in the sample was measured by in-line SEC and py-GC/MS analysis system.

Figure 1:
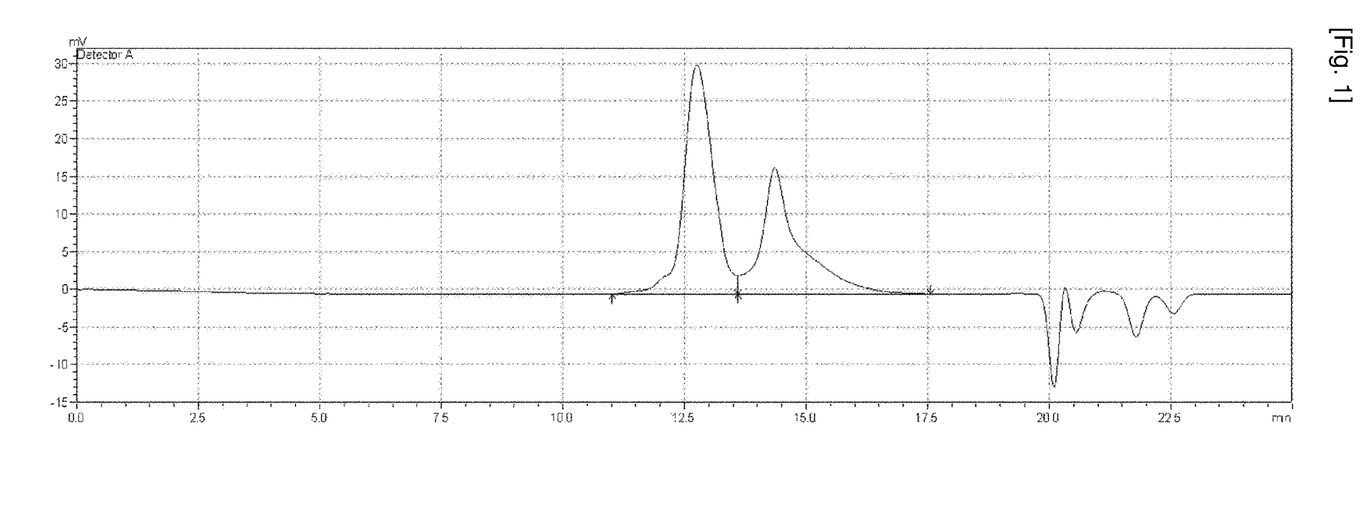
FIGS. 1 and 2 illustrate a chromatogram obtained by analyzing a sample to be analyzed by size exclusion chromatography (SEC) and determining a collecting range based on the chromatogram, according to an embodiment of the present invention.
Figure 2:
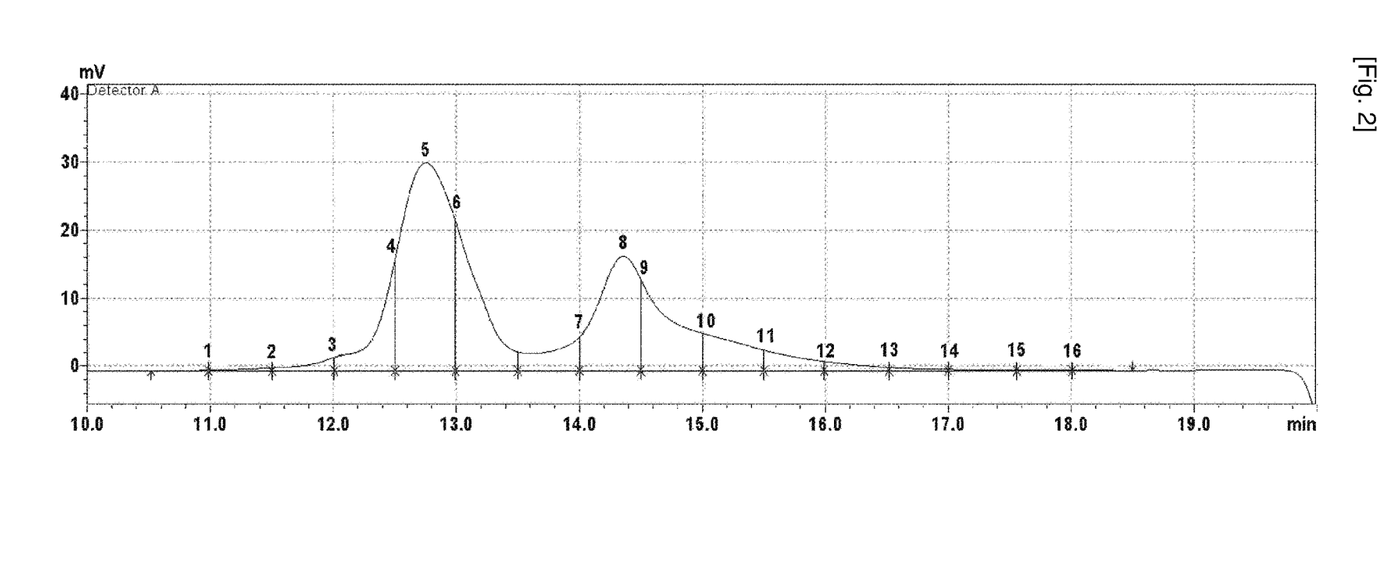
Figure 3A:
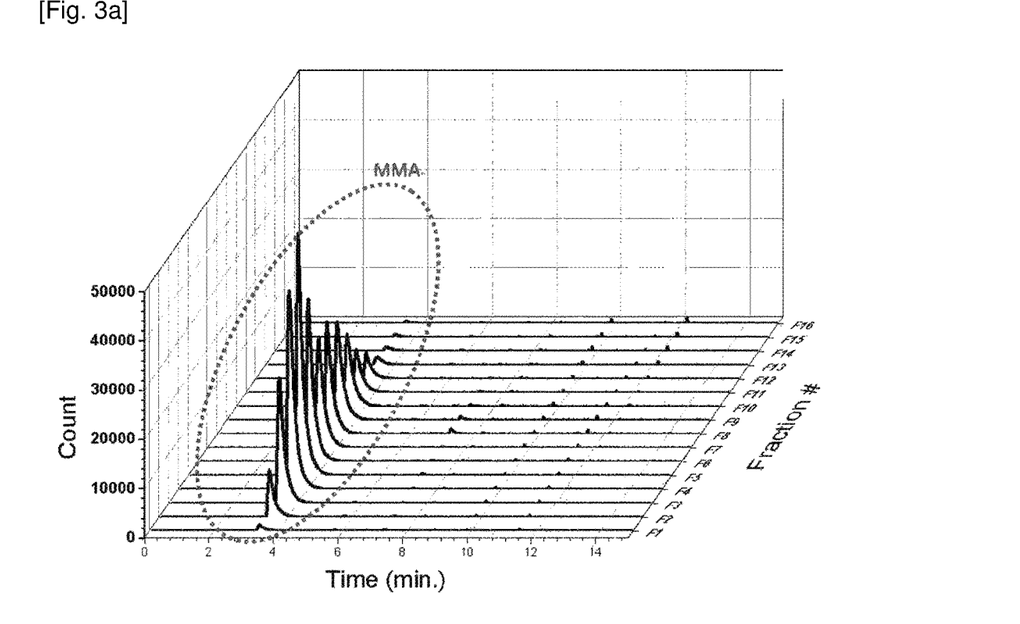
FIGS. 3a and 3b illustrate mass spectra obtained by analyzing each sample collected from size exclusion chromatography (SEC) by pyrolysis-gas chromatography-mass spectrometry (Py-GC/MS), according to an embodiment of the present invention.
Figure 3B:
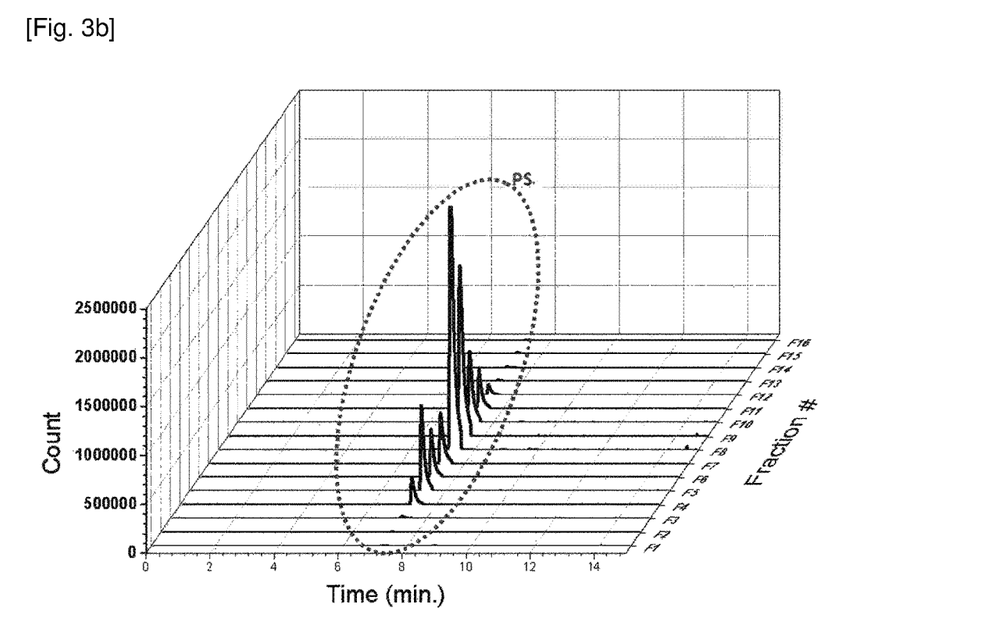

First, the colleting range was designated based on the chromatogram (see FIG. 1) obtained by injecting the sample into size exclusion chromatography (SEC) (see FIG. 2). The sample was automatically collected by PAL RTC from CTC Analytics (Swiss) at 30 second intervals and directly injected into pyrolysis-gas chromatography-mass spectrometer (Py-GC/MS), thereby obtaining mass spectrum of each of the collected samples. Mass spectral data at 100 and 104 mass/charge (m/z) were extracted based on MMA and styrene (PS) which are monomers of the sample (see FIGS. 3a and 3b).

The sum of areas from the height of each peak of mass spectrum is set to 100 and the monomer content ratio is set to 50:50 as the monomer content ratio of the standard product. The relative content ratio of monomer for each fraction is calculated to perform peak area normalization. The calculated relative content ratio of monomer is as follows.

TABLE 1

| Fraction # | Styrene(%) | MMA(%) |
|---|---|---|
| F1 | <0.1 | 0.3 |
| F2 | <0.1 | 1.7 |
| F3 | 0.2 | 5.0 |
| F4 | 1.7 | 8.9 |
| F5 | 5.3 | 10.6 |
| F6 | 3.0 | 6.7 |
| F7 | 3.2 | 4.6 |
| F8 | 17.9 | 3.8 |
| F9 | 10.6 | 3.4 |
| F10 | 4.5 | 2.1 |
| F11 | 2.6 | 1.4 |
| F12 | 0.7 | 1.1 |
| F13 | 0.1 | 0.1 |
| F14 | 0.1 | 0.2 |
| F15 | 0.1 | 0.1 |
| F16 | <0.1 | <0.1 |
| Total | 50 | 50 |

Figure 4:
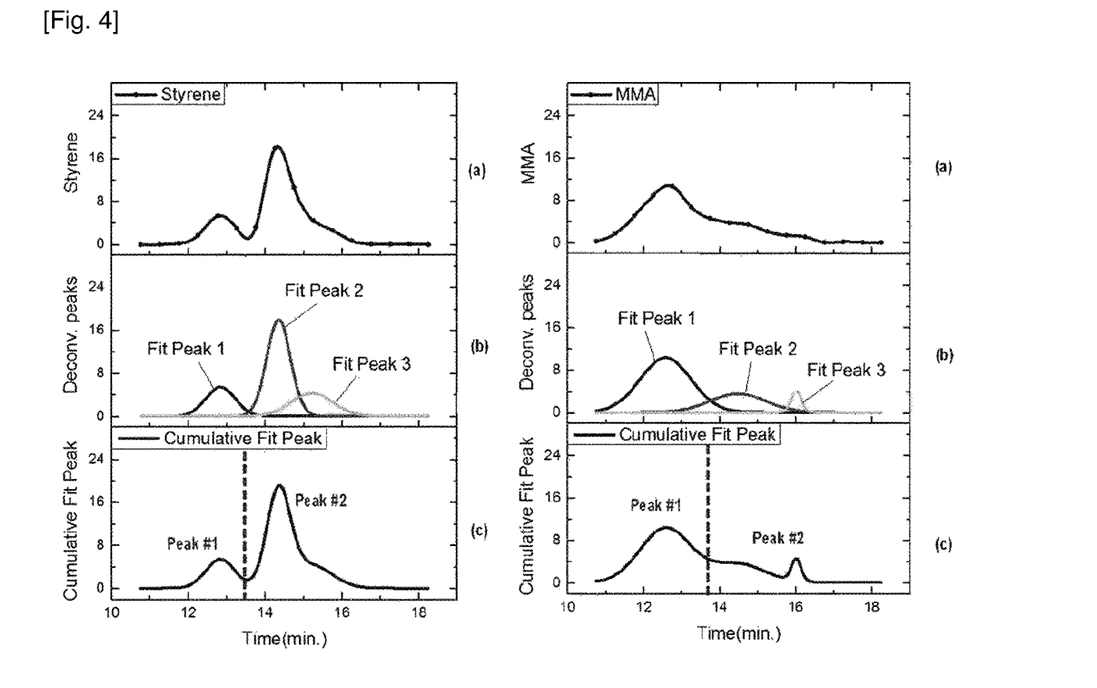
FIG. 4 illustrates graphs showing a procedure of obtaining molecular weight of unit polymer contained in a sample according to an embodiment of the present invention.

The relative content ratio of monomer in Table 1 was used as a raw data (see, graph (a) in FIG. 4).

Next, with the Origin program (version 9.1) of OriginLab Corporation, peak points of the raw data (see graph (a) in FIG. 4) were subjected to deconvolution to a probability density function of Gaussian distribution according to Equation 1 below (see graph (b) in FIG. 4) to prepare a cumulative fit peak chromatogram, in which three main peaks were distributed into two peaks (see graph (c) in FIG. 4). For the two peaks, the molecular weight of each of the unit polymers was calculated by substituting into the calibration curve obtained from the analysis of a standard for analysis of relative molecular weight by SEC.

$$f(x|\mu, \sigma^2) = \frac{1}{\sqrt{2\pi\sigma^2}} e^{-\frac{(x-\mu)^2}{2\sigma^2}}$$ [Equation 1]

In Equation 1,
μ is a mean,
σ is a standard deviation,
$\sigma^2$ is a variance.

The molecular weight of PMMA and PS obtained in this example is shown in Tables 2 and 3 below, respectively. Table 2 shows calculation results of the molecular weight of polystyrene (PS), and Table 3 shows calculation results of the molecular weight of polymethylmethacrylate (PMMA).

TABLE 2

|  | Mn | Mw | PDI(Mw/Mn) |
|---|---|---|---|
| total | 53809 | 279999 | 5.2 |
| Peak 1 | 760638 | 1008274 | 1.3 |
| Peak 2 | 43357 | 91493 | 2.1 |

TABLE 3

|  | Mn | Mw | PDI(Mw/Mn) |
|---|---|---|---|
| Total | 48502 | 699401 | 14.4 |
| Peak 1 | 852112 | 1462953 | 1.7 |
| Peak 2 | 27701 | 91447 | 3.3 |

As can be seen from the results of Table 2 and Table 3, it is possible to calculate the molecular weight of each of high molecular weight (about 1 million Daltons) PMMA and PS in Peak 1 and to calculate the molecular weight of each of low molecular weight (about 100,000 Daltons) PMMA and PS in Peak 2.

From this example, it can be seen that according to the analysis method using the analysis system according to the present invention, molecular weight distribution and molecular weight of each of unit polymers can be analyzed concurrently for the polymer compound in which polymers of various molecular weights are blended.

COMPARATIVE EXAMPLE

The same sample to be analyzed as used in Example 1 was analyzed by size exclusion chromatography and by pyrolysis gas chromatography-mass spectrometry, respectively.

Figure 5:
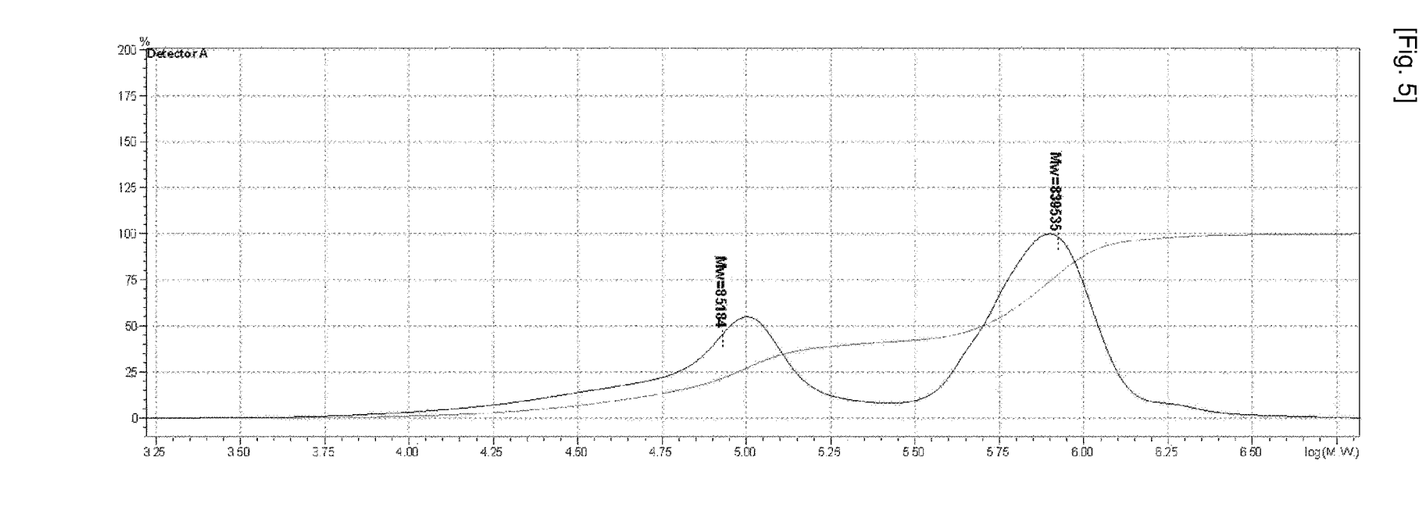
FIG. 5 illustrates an analysis result of molecular weight by size exclusion chromatography (SEC) according to a conventional method, for the same sample as in Example.
Figure 6:
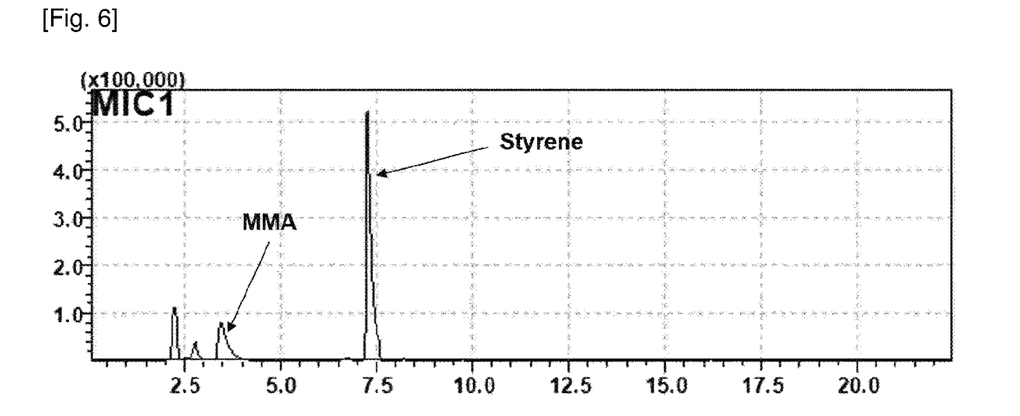
FIG. 6 illustrates an analysis result of pyrolysis gas chromatography (Py-GC)-mass spectrometer (MS) according to a conventional method, for the same sample as in Example.

The results of analysis by size exclusion chromatography alone are the same as in FIG. 1, from which the result of analyzing the molecular weight of the sample is shown in FIG. 5, where only the overall molecular weight distribution of the sample can be determined. In addition, FIG. 6 shows the results of analysis by pyrolysis gas chromatography-mass spectrometry, where only the total content of monomers contained in the sample can be identified.

The molecular weight and molecular weight distribution of the sample obtained in this comparative example are shown in Table 4 below.

TABLE 4

|  | Mn | Mw | PDI(Mw/Mn) |
|---|---|---|---|
| total | 90135 | 528616 | 5.9 |
| Peak 1 | 699554 | 844238 | 1.2 |
| Peak 2 | 40507 | 84723 | 2.1 |

In this comparative example, it can be seen that there is a limit that cannot separately analyze the molecular weight of each of the PMMA and PS contained in the sample.

As can be seen from the above example and comparative example, according to the present invention, for a mixture of two or more kinds of unit polymers having different molecular weight, it was possible to concurrently determine molecular weight distribution of each unit polymer and calculate the molecular weight of each unit polymer with a single sample by using in-line size exclusion chromatography-pyrolysis gas chromatography-mass spectrometry analysis system.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. An analysis method of molecular weight of unit polymer contained in a polymer compound, comprising:

(A) injecting a sample of the polymer compound into size exclusion chromatography (SEC), and collecting the sample passed through the size exclusion chromatography at a predetermined time interval;

(B) introducing the sample collected in (A) directly into pyrolysis gas chromatography (Py-GC)-mass spectrometry (MS) which is connected to the size exclusion chromatography, thereby obtaining a mass spectrum;

(C) normalizing each peak area of the mass spectrum obtained in (B) to obtain a relative content ratio of monomer constituting the unit polymer;

(D) obtaining from a relative content ratio of monomer a graph of relative content ratio according to collection time as a raw data;

(E) deconvoluting peak points of the raw data to a probability density function of Gaussian distribution to obtain a deconvolution graph; and (F) obtaining a cumulative fit peak chromatogram from the deconvolution graph and substituting the cumulative fit peak chromatogram into a calibration curve of a standard to calculate molecular weight of each unit polymer.

2. The analysis method of molecular weight of unit polymer contained in a polymer compound according to claim 1, wherein the normalization (C) comprises analyzing the sample to obtain a total content ratio of monomers, and to determine a relative content ratio from the relative area of each peak based on the total content ratio of monomers when a sum of peak areas of the mass spectrum obtained in (B) is set to 100.

3. The analysis method of molecular weight of unit polymer contained in a polymer compound according to claim 1, wherein the sample in (A) is automatically collected at an interval of from 5 seconds to 600 seconds.

4. The analysis method of molecular weight of unit polymer contained in a polymer compound according to claim 1, wherein the unit polymer contained in the polymer compound in (A) comprises two or more polymers having a different weight average molecular weight or a number average molecular weight.

5. The analysis method of molecular weight of unit polymer contained in a polymer compound according to claim 1, wherein the unit polymer contained in the polymer compound in (A) is a homopolymer or a copolymer.

6. The analysis method of molecular weight of unit polymer contained in a polymer compound according to claim 1, wherein the unit polymer in (A) has a bimodal or multimodal molecular weight distribution.

7. The analysis method of molecular weight of unit polymer contained in a polymer compound according to claim 1, wherein oxygen-containing organic compounds are used at a flow rate of 0.005 to 10 mL/min as a mobile phase of size exclusion chromatography in (A).

8. The analysis method of molecular weight of unit polymer contained in a polymer compound according to claim 7, wherein the mobile phase is tetrahydrofuran (THF).

9. The analysis method of molecular weight of unit polymer contained in a polymer compound according to claim 1, wherein Ar or He is used as a carrier gas in (B).

10. The analysis method of molecular weight of unit polymer contained in a polymer compound according to claim 1, the pyrolysis in (B) is performed at 500 to 800° C. at a temperature increase rate of 50 to 80° C./sec.

11. An analysis system used in the analysis method according to claim 1, comprising:
a size exclusion chromatography into which the sample is injected;
a sample collection and injection device configured to automatically collect the sample passed through the size exclusion chromatography at a predetermined time interval and injecting the sample into a subsequent device;
a pyrolyzer in which the collected sample is injected and pyrolyzed; and
a gas chromatograph and mass spectrometer into which the pyrolyzed sample is injected.

12. The analysis system according to claim 11, wherein the size exclusion chromatograph comprises a column having a length of 30 to 100 mm and an inner diameter of 5 to 10 mm and filled with particles having a particle diameter of 5 to 20 μm, and a column having a length of 400 to 500 mm and an inner diameter of 5 to 10 mm and filled with particles having a particle diameter of 5 to 20 μm.

13. The analysis system according to claim 11, wherein the gas chromatograph comprises a column having a length of 20 to 50 m, an inner diameter of 0.1 to 0.5 mm, and a thickness of 0.1 to 0.5 μm.

\* \* \* \* \*